United States Patent [19]

DesMarteau et al.

[11] Patent Number: 5,081,299
[45] Date of Patent: Jan. 14, 1992

[54] FLUORINATED ALKOXYIMINES AND THEIR N-CHLORO- AND N-BROMO-DERIVATIVES, AND PROCESS FOR THEIR PREPARATION

[75] Inventors: Darryl D. DesMarteau; Stefan P. Kotun, both of Clemson, S.C.

[73] Assignee: Ausimont S.r.l., Milan, Italy

[21] Appl. No.: 692,960

[22] Filed: Apr. 26, 1991

Related U.S. Application Data

[63] Continuation of Ser. No. 388,406, Aug. 2, 1989, abandoned.

Foreign Application Priority Data

Aug. 3, 1988 [IT] Italy ................. 21627 A/88

[51] Int. Cl.$^5$ ............................ C07C 251/52
[52] U.S. Cl. ........................ 564/256; 564/301
[58] Field of Search ........................ 564/256

[56] References Cited

U.S. PATENT DOCUMENTS 2,770,652 11/1956 England .................. 564/256
3,655,758 4/1972 Kurhajec et al. ........... 564/256

OTHER PUBLICATIONS

Koslyanovskii et al., Bull. Acad. Science U.S.S.R, vol. 23, pp. 1537–1539 (1975).
Chemical Abstracts, vol. 96, No. 3, 01/18/82, p. 404, Abstract No. 19610C (W. Y. Lam, et al.).

*Primary Examiner*—James H. Reamer
*Attorney, Agent, or Firm*—Morgan & Finnegan

[57] ABSTRACT

Novel fluorinated alkoxy imines having the formula:

$$R_x-CF=N-O-CZ_1Z_2-CF_3 \qquad (I)$$

wherein:

$R_x$ is either F or a perhalogenated alkyl group containing from 1 to 3 carbon atoms, and $Z_1$ and $Z_2$, either equal to, or different from, each other, are F, Cl, Br, H or a perfluorinated alkyl group containing 1 to 3 carbon atoms. They are prepared by reacting a fluorinated alkoxy-amine having the formula:

$$R_x-CF_2-NH-O-CZ_1Z_2-CF_3 \qquad (V)$$

with KF at a temperature within the range of from 0° to 100°C.

Furthermore, N-chloro- and N-bromo-derivatives of said fluorinated alkoxy-imines (I) are provided, which derivatives have the formulae:

$$R_x-CF_2-NCl-O-CZ_1Z_2-CF_3 \qquad (VII)$$

and $$R_x-CF_2-NBr-O-CZ_1Z_2-CF_3 \qquad (VIII)$$

3 Claims, No Drawings

FLUORINATED ALKOXYIMINES AND THEIR N-CHLORO- AND N-BROMO-DERIVATIVES, AND PROCESS FOR THEIR PREPARATION

This is a continuation of co-pending application Ser. No. 388,406, filed on Aug. 2, 1989, now abandoned.

DESCRIPTION OF THE INVENTION

The present invention relates to new fluorinated alkoxy imines, and to a process for their preparation. It relates also to new N-chloro and N-bromo-derivatives of the said alkoxy imines, and to their preparation.

Another object is to provide new N-chloro- and N-bromo-derivatives of said fluorinated alkoxy imines.

A further object is to provide a process for the preparation of said fluorinated alkoxy imines.

Still another object is to provide a process for preparing the N-chloro, N-bromo-, and N-fluoro-derivatives of said fluorinated alkoxy imines.

According to the first object of the present invention, a new class is provided of fluorinated alkoxy-imines having the formula:

$$R_x\text{---}CF\text{=}N\text{---}O\text{---}CZ_1Z_2\text{---}CF_3 \quad (I)$$

wherein $R_x$ is either F or a perhalogenated alkyl group containing from 1 to 3 carbon atoms, and $Z_1$ and $Z_2$, either equal to, or different from, each other, are F, Cl, Br, H or a perfluorinated alkyl group containing from 1 to 3 carbon atoms.

$R_x$ is preferably either F or a perfluorinated alkyl group containing from 1 to 3 carbon atoms.

The preferred fluorinated alkoxy-imines belong to the class of formula $$CF_2\text{=}N\text{---}O\text{---}CFZ\text{---}CF_3 \quad (I')$$

wherein Z represents F, Cl or H.

The following compounds belong to class (I'):

a) $CF_2\text{=}N\text{---}O\text{---}CF_2\text{---}CF_3$ (II)

(pentafluoroethoxy)-carbonimide difluoride, b) $CF_2\text{=}N\text{---}O\text{---}CFCl\text{---}CF_3$ (III)

(1-chloro-1,2,2,2-tetrafluoroethoxy)-carbonimide difluoride, and c) $CF_2\text{=}N\text{---}O\text{---}CFH\text{---}CF_3$ (IV)

(1,2,2,2-tetrafluoroethoxy)-carbonimide difluoride.

The starting compounds for preparing the fluorinated alkoxy imines (I) are the fluorinated alkoxy amines having the formula:

$$R_x\text{---}CF_2\text{---}NH\text{---}O\text{---}CZ_1Z_2\text{---}CF_3 \quad (V)$$

The fluorinated alkoxy amines (V), and a process for preparing them are disclosed in a co-pending Italian patent application No. 21615 A/88.

According to said process, a fluorinated oxazetidine

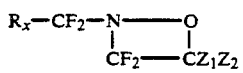
(VI)

is reacted, at a temperature within the range of from $-80°$ to $+300°$ C. with HF, in the presence of a Lewis acid, preferably $AsF_5$.

According to the process of the present invention, a fluorinated alkoxy amine $$R_x\text{---}CF_2\text{---}NH\text{---}O\text{---}CZ_1Z_2\text{---}CF_3 \quad (V)$$

is reacted with KF at a temperature within the range of from 0° to 100° C.

A dehydrofluorination reaction takes place, whereby a fluorinated alkoxy imine (I) is produced.

The temperature is preferably within the range of from 25° to 50° C.

The molar ratio of KF to the alkoxy amine (V) is commonly within the range of from 5 to 50, and preferably of from 5 to 15.

The reaction times are usually within the range of from 0.5 hours to 30 hours, and, more frequently, of from 0.5 to 1 hour.

The fluorinated alkoxy imines (I) may be converted into their corresponding N-chloro-, N-bromo- and N-fluoro-derivative by an halogenation reaction, as disclosed in the following:

The compounds obtained are:

$$R_x\text{---}CF_2\text{---}NCl\text{---}O\text{---}CZ_1Z_2\text{---}CF_3 \quad (VII)$$

$$R_x\text{---}CF_2\text{---}NBr\text{---}O\text{---}CZ_1Z_2\text{---}CF_3 \quad (VIII)$$

$$R_x\text{---}CF_2\text{---}NF\text{---}O\text{---}CZ_1Z_2\text{---}CF_3 \quad (IX)$$

The compounds of classes (VII) and (VIII) are new, and are a further object of the present invention.

The preferred compounds belonging to classes (VII) and (VIII) are:

$$CF_3\text{---}NCl\text{---}O\text{---}CFZ\text{---}CF_3 \quad (VII')$$

$$CF_3\text{---}NBr\text{---}O\text{---}CFZ\text{---}CF_3 \quad (VIII')$$

wherein Z stands for F, Cl or H.

To the class (VII') the following compounds belong:

a') $CF_3\text{---}NCl\text{---}O\text{---}CF_2CF_3$ (X)

(1,1,1-trifluoro-N-chloro-N-(pentafluoroethoxy)-methaneamine, b') $CF_3\text{---}NCl\text{---}O\text{---}CFClCF_3$ (XI)

(1,1,1-trifluoro-N-chloro-N-(1-chloro-1,2,2,2-tetrafluoroethoxy)-methane-amine, and c') $CF_3\text{---}NCl\text{---}O\text{---}CFHCF_3$ (XII)

(1,1,1-trifluoro-N-chloro-N-(1,2,2,2-tetrafluoroethoxy)-methane-amine.

To the class (VIII') the following compounds belong:

a'') $CF_3\text{---}NBr\text{---}O\text{---}CF_2CF_3$ (XIII)

(1,1,1-trifluoro-N-bromo-N-(pentafluoroethoxy)-methaneamine, b'') $CF_3\text{---}NBr\text{---}O\text{---}CFClCF_3$ (XIV)

(1,1,1-trifluoro-N-bromo-N-(1-chloro-1,2,2,2-tetrafluoroethoxy)-methane-amine, and c") $CF_3-NBr-O-CFHCF_3$ (XV)

(1,1,1-trifluoro-N-bromo-N-(1,2,2,2-tetrafluoroethoxy)-methane-amine.

The fluorinated alkoxy imines (I) are useful as monomers; they are also useful intermediates for the preparation of their N-chloro-, N-bromo- and N-fluoroderivatives.

The N-chloro-derivatives (VII), and the N-bromoderivatives (VIII) are useful as telogens. The N-fluoroderivatives (IX) are useful as catalysts for $C_2F_4$ polymerization.

The fluorinated alkoxy imines (I) may be chlorofluorinated to yield their corresponding N-chloro-derivatives, as follows: a fluorinated alkoxy imine having the formula:

$$R_x-CF=N-O-CZ_1Z_2-CF_3 \quad (I)$$

is reacted with ClF at a temperature within the range of from $-160°$ to $+25°$ C. The reaction may be carried out in the presence of a catalyst, which is a fluoride of an alkali metal, or of an alkaline-earth metal.

The catalyst is preferably CsF, RbF or KF, and, still more preferably, CsF.

The preferred reaction temperature is usually within the range of from $-100°$ to $+25°$ C.

The molar ratio of ClF to the alkoxy imine (I) is usually within the range of from 1 to 2 and, still more usually, within the range of from 1.0 to 1.2.

The molar ratio of the catalyst, computed as CsF, to the alkoxyimine (I) is commonly within the range of from 0.5 to 100, and, still more commonly, within the range of from 5 to 10.

The fluorinated alkoxy imines (I) may be bromofluorinated to yield their corresponding N-bromoderivatives as follows: a fluorinated alkoxy imine having the formula:

$$R_x-CF=N-O-CZ_1Z_2-CF_3 \quad (I)$$

is reacted at a temperature within the range of from $-60°$ to $+30°$ C. with $Br_2$ and a fluoride of an alkali metal or of an alkaline-earth metal.

The preferred reaction temperature is usually within the range of from $0°$ to $30°$ C.

The metal fluoride is preferably CsF, RbF or KF, or, more preferably, by CsF.

The molar ratio of $Br_2$ to the alkoxy imine (I) is usually within the range of from 1 to 100, and, still more usually, within the range of from 3 to 10.

The molar ratio of the metal fluoride, computed as CsF, to the alkoxy imine (I) is usually within the range of from 2 to 100, and, still more usually, within the range of from 10 to 20.

The fluorinated alkoxy imines (I) may be fluorinated to yield their corresponding N-fluoro-derivatives as follows: a fluorinated alkoxy imine having the formula:

$$R_x-CF=N-O-CZ_1Z_2-CF_3 \quad (I)$$

is reacted with $F_2$ at a temperature within the range of from $-196°$ to $+25°$ C.

The reaction is optionally carried out in the presence of a catalyst selected from the group consisting of the fluorides of the alkali metals, and of the fluorides of the alkaline-earth metals.

The preferred reaction temperature is usually within the range of from $-80°$ to $+25°$ C.

The catalyst is preferably CsF, RbF or KF, and, still more preferably, CsF.

The molar ratio of $F_2$ to the alkoxy imine (I) is usually within the range of from 1 to 2 and, still more usually, within the range of from 1.0 to 1.2.

The molar ratio of the catalyst, computed as CsF, to the alkoxy-imine (I) is commonly within the range of from 0.5 to 100, and, still more usually, within the range of from 5 to 10.

The above reactions of chlorofluorination, bromofluorination and fluorination of the alkoxy imines (I) may be carried out in suitable solvents compatible with the reactants and with the reaction products.

Examples

The following examples still further illustrate the inventive concept of the present invention.

EXAMPLE 1

This example describes the preparation of $$CF_2=N-OCF_2-CF_3$$

by starting from $CF_3-NH-OCF_2-CF_3$.

Potassium fluoride (Aldrich) was dried and activated by melting it in a platinum crucible, and subsequently grinding it in a ball-mill under a dry nitrogen atmosphere.

KF was stored, and weighed inside the reactor in a "dry box", filled with nitrogen.

The reactor consisted of a Hoke 304 bomb of stainless steel of 75 ml of capacity, provided with a Nupro SS-4JBR valve. Then, inside the bomb KF (1.15 g, 19.8 mmol) was weighed in the "dry box", together with three steel bearing balls.

To the reaction bomb, vacuum (5 microns Hg) was applied, and 2.70 mmol of $$CF_3-N(H)-OCF_2-CF_3$$

was condensed under static vacuum conditions (5 microns Hg), by means of a vacuum line of Pyrex glass, while the reaction bomb was kept at the temperature of $-196°$ C.

The reactor temperature was increased up to 24° C., and the reactor was left standing, with occasional shaking, for 16 hours. The volatile contents of the bomb were then pumped inside a "U"-shaped trap, cooled with liquid nitrogen, and fractionated under dynamic vacuum (5 microns Hg), through traps kept cooled at $-50°$ C., $-90°$ C., and $-196°$ C.; inside the trap at $-90°$ C., 2.49 mmol (yield 92.2%) of $$CF_2=N-O-CF_2-CF_3$$

was collected.

This compound was characterized by IR, $^{19}F$-NMR and mass spectrum.

For the IR characterization, a Perkin-Elmer 1430 apparatus equipped with a 7500 data station was used. The spectra were obtained in the gas phase with a 10-cm cell, provided with KCl windows attached with Halocarbon 1500 wax.

For the N.M.R. characterization, an IBM NR 200AF apparatus was used, operating at 200.13 MHz for $^1H$ and at 188.31 MHz for $^{19}F$.

The downfield chemical shifts from internal $(CH_3)_4Si$ and $CFCl_3$, respectively, are reported as positive.

As regards the mass spectrum characterization, a Hewlett-Packard 5985 B apparatus, operating at 70 eV, was used. As the CI gas, $CH_4$ was used. The temperatures were measured with a thermocouple of J type.

The same characterization procedure was followed in Examples 2, 3, 4 and 5.

IR (4 torr): 5(vw), 2742(vw), 1969(vw), 1850(vw), 1755($v_{C=N}$,vs), 1394(sh,m), 1375(vs), 1237(vs), 1216(vs), 1195(s), 1108(vs), 1035(s), 926(vw), 848(m), 812(vw), 744(m), 726(sh,w), 645(w), 527(w) cm$^{-1}$; wherein:

m=medium; sh=shoulder; w=weak; s=strong; vs=very strong; and vw=very weak.

$^{19}F$-NMR $F^AF^XC=N-OCF_2{}^BCF_3{}^C$ (CDCl$_3$, 24° C.) δA −54.1 (1F,br d), X −85.1 (1F, br d), B −93.9 (2F, d-q), C −84.8 ppm (3F, t), $J_{AX}=63.6$, $J_{BX}=2.6$, $J_{BC}=1.6$, $J_{AB}=J_{AC}=J_{CX}=0$ Hz.

Mass spectrum major m/z (EI): 199 (M+), 180 (M-F+), 130 (CF$_2$=NOCF$_2$+), 119 (CF$_2$CF$_3$+, 69 (CF$_3$+), 64 (CF$_2$=N+), 50 (CF$_2$+), 47 (FCO+);

major m/z (CI): 200 (M+1+), 180 (M+1-HF+), 130 (CF$_2$=NOCF$_2$+), 119 (CF$_3$CF$_2$+).

EXAMPLE 2

This example describes the preparation of

CF$_2$=N—OCFCl—CF$_3$ by starting from CF$_3$—NH—OCFCl—CF$_3$.

Potassium fluoride (Aldrich) was melted as received. It was stored and weighed inside the reactor in a "dry box" filled with nitrogen.

The reactor consisted of a Hoke 304 bomb of stainless steel of 75 ml capacity, provided with a Nupro SS-4JBR valve. Then, KF (2.25 g, 38.7 mmol) was weighed inside the reactor in the "dry box", with two steel bearing balls of ⅜ inch diameter being added.

To the bomb, vacuum (5 microns Hq) was then applied, and subsequently 3.87 mmol of CF$_3$—N(H)—OCFCl—CF$_3$ was added through a Pyrex vacuum line, under static vacuum conditions (5 microns Hg), while the reactor was kept at the temperature of −196° C.

The temperature of the reaction bomb was increased up to 24° C., and the bomb was then placed inside an oil bath with stirring, at the temperature of 60° C., for 12 hours; during this time period, the reactor was periodically withdrawn from the oil bath in order to shake it.

After allowing the reactor to cool down to 24° C., the volatile contents of the bomb were subsequently pumped inside a "U"-shaped trap of Pyrex, cooled with liquid nitrogen, and fractionated under dynamic vacuum (5 microns Hg), through a series of traps kept cooled at −70° C., −120° C., and −196° C.; inside the trap at −120° C.,

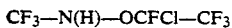
CF$_2$=N—OCFCl—CF$_3$ was collected (2.12 mmol; yield 54.8%).

This compound was characterized as follows:

IR (4 torr): 2778(vw), 2742(vw), 1751($v_{C=N}$,vs), 1375(vs), 1331(s), 1286(sh,vw), 1231(vs), 1155(vs), 1098(vs) 1032(s), 998(vs), 946(vw), 912(m), 863(vw), 828(w), 768(m), 727(m), 700(sh,w), 642(m), 606(vw), 530(m) cm$^{-1}$;

$^{19}F$—NMR $F^AF^XC=N-OCF_2{}^BClCF_3{}^C$ (CDCl$_3$, 24° C.) δA −53.9 (1F,d-d), X −84.5 (1F, br d), B −79.9 (1F, q-t), C −83.2 ppm (3F, d), $J_{AX}=63.8$, $J_{AB}=J_{BX}=1.8$, $J_{BC}=3.0$, $J_{AC}=J_{CX}=0$ Hz.

Mass spectrum major m/z (EI): 215/217 (M+), 196/198 (M-F+), 180(M-Cl+), 146/148 (M-CF$_3$+), 135/137 (CF$_3$CFCl+), 130 (M-CF$_2$Cl+), 85/87 (CF$_2$Cl+), 69 (CF$_3$+), 64 (CF$_2$=N+), 50 (CF$_2$+), 47 (COF+);

major m/z (CI): 216/218 (M+1+), 196/198 (M+1-HF+), 180 (M+1-HCl+), 146/148 (M-CF$_3$+), 135/137 (CF$_3$CFCl+), 130 (M-CF$_2$Cl+).

EXAMPLE 3

This example describes the preparation of:

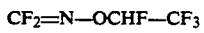
CF$_2$=N—OCHF—CF$_3$ by starting from CF$_3$—NH—OCHF—CF$_3$.

The preparation of CF$_2$=N—OCHF—CF$_3$ was carried out by using exactly the same operating procedure as previously adopted for CF$_2$=N—OCFCl—CF$_3$, with the following modifications:

| | |
|---|---|
| CF$_3$—N(H)—OCHF—CF$_3$: | 2.71 mmol |
| KF amount: | 1.10 g (19.0 mmol) |
| Reaction time at 60° C.: | 17 hours. |

Fractionation: traps at −80° C., −120° C. and −196° C.

CF$_2$=N—OCHF—CF$_3$ (2.00 mmol) was collected inside the trap at −120° C., with a yield of 73.8%.

CF$_2$=N—OCHF—CF$_3$ was characterized as follows: IR (3 torr): 2998($v_{C-H}$,m), 1750($v_{C-N}$,vs), 1705(sh,vw), 1441(vw), 1412(m), 1369(vs), 1329(vw), 1290(s), 1250(w), 1214(vs), 1192(vs), 1143(vs), 1091(s), 1027(s), 961(m), 928(vw), 903(vw), 872(m), 729(m), 677(m), 637(w), 602(sh,vw), 584(sh,vw), 566(w), 534(w) cm$^{-1}$.

$^{19}F$—NMR $F^AF^XC=N-OCHF^BCF_3{}^D$ (CDCl$_3$, 24° C.): $^1H$ δ5,8 (d-q-t), $^{19}F$ δA −56.1 (1F,d-d), X −87.7 (1F, br d), B −143.8 (1F, d-q-d-d), D −82.4 ppm (3F, d-d), $J_{HA}=J_{HX}=0.6$, $J_{HB}=57.6$, $J_{HC}=3.2$, $J_{AX}=57.6$, $J_{AB}=3.0$, $J_{BX}=0.6$, $J_{BC}=6.1$, $J_{AC}=J_{CX}=0$ Hz.

Mass spectrum: major m/z (EI): 181 (M+), 162 (M-F+), 112 (M-CF$_3$+), 101 (CF$_3$CHF+), 69 (CF$_3$+), 64 (CF$_2$=N+), 50 (CF$_2$+); major m/z (CI): 182 (M+1+), 162 (M+1-HF+), 112 (M-CF$_3$+).

EXAMPLE 4

This example describes the preparation of

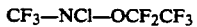
CF$_3$—NCl—OCF$_2$CF$_3$ by starting from CF$_2$=N—OCF$_2$CF$_3$ and ClF.

The reactor consisted of a Hoke 304 bomb of stainless steel of 75 ml of capacity, equipped with a Nupro SS+4JBR valve.

To the bomb vacuum was applied (5 microns Hg) and the metal vacuum line, as well as the bomb, was treated with four successive portions of ClF$_3$ gas (100 torr), with ClF$_3$ gas being added to the system under vacuum, and being allowed to rest at the temperature of 22° C., each time for about 10 minutes.

The bomb was evacuated and cooled down to −196° C., and 0.61 mmol of

was condensed under static vacuum conditions (5 microns Hg); subsequently, 0.79 mmol of ClF was charged.

The temperature of the bomb was then allowed to slowly increase inside a Dewar bottle, initially at −196° C. 9.5 hours later, the temperature was 15° C., and the bomb was removed from the Dewar bottle and was left standing half an hour at the temperature of 22° C.

The reactor was then cooled down to −120° C., and any volatiles at this temperature were then removed under dynamic vacuum (5 microns Hg). The residual matter was then fractionated by pumping through a series of cold traps kept cooled at the temperatures of −55° C., −100° C., and −196° C.

0.57 mmol (yield: 94%) of $CF_3-N(Cl)OCF_2-CF_3$ was collected inside the separator at −100° C.

$CF_3-N(Cl)OCF_2-CF_3$ was characterized as follows:

IR (2 torr): 2047(vw), 1875(vw), 1392(m), 1276(vs), 1243(vs), 1218(s), 1187(vs), 1097(vs), 953(w), 879(m), 853(w), 798(vw), 766(w), 741(m), 693(vw), 672(m), 523(w) cm$^{-1}$.

$^{19}F$—NMR $CF_3{}^C N(Cl)-OCF^A F^B CF_3{}^{CD}$ (CDCl$_3$, 24° C.) δA −94.3, B −97.6 (2F, rather broad typical AB) pattern, C −76.5 (3F, t), D −84.8 ppm (3F, t), $J_{AB}=144$, $J_{AC}=J_{BC}=2.7$, $J_{AD}=J_{BD}=1.7$, $J_{CD}=0$ Hz.

Mass spectrum major m/z (EI): 219 (M-Cl$^+$), 131 ($CF_2=NOCF_2{}^+$), 119 ($CF_2CF_3{}^+$), 100 ($CF_3CF^+$), 99 ($CF_3NO^+$), 83 ($CF_3N^+$), 69 ($CF_3{}^+$), 64 ($CF_2=N^+$), 50 ($CF_2{}^+$); major m/z (CI): 254/256 (M+1$^+$), 234/236 (M+1-HF$^+$), 219 (M+1-Cl$^+$), 218 (M+1-HCl$^+$), 180 (FCN—OC$_2$F$_5{}^+$), 135 ($CF_3CF_2O^+$), 130 ($CF_2=NOCF_2{}^+$), 119 ($CF_3CF_2$).

EXAMPLE 5

This example describes the preparation of

by starting from $CF_2=N-OCF_2CF_3$, Br$_2$ and CsF.

Cesium fluoride (Cabot) was dried and activated by melting inside a platinum crucible, followed by grinding inside a ball mill under a dry nitrogen atmosphere; CsF was handled and weighed inside the reactor in a nitrogen-filled "dry box".

Bromine (Fisher) was stored over P$_4$O$_{10}$, inside a bulb provided with a glass/Teflon ® stopcock.

The reactor was constituted by a bulb of 50 ml capacity inside a screw-top fitting ("Ace-Thred", Ace Glass Co.), which was tightly sealed by means of an O-ring compressed by a Teflon ® insulating gasket, through which a tube protruded, on which a glass/Teflon ® stopcock was connected.

CsF (0.76 g, 5.0 mmol) was weighed inside the reactor in the "dry box", and a Teflon ®-coated magnetic stirring bar was added.

The bulb was then put under vacuum (5 microns Hg, with the same vacuum being applied in all of the subsequent operating steps to be conducted under vacuum), and 7.00 mmol of bromine was condensed by static vacuum, through a Pyrex vacuum line, with the reactor being maintained at the temperature of −196° C. The CsF/Br$_2$ mixture was stirred, at 22° C., for 4 hours.

The reactor was cooled again with liquid nitrogen, and $CF_2=N-OCF_2CF_3$ (1.00 mmol) was added through the glass line, under static vacuum, by operating in the dark. The reactor was heated to the temperature of 22° C, wrapped inside an aluminum foil, and kept 16 hours with stirring.

The volatile matters were then pulled into a "U"-shaped Pyrex trap cooled with liquid nitrogen. Ethylene (Matheson C.P., 3.00 mmol) was allowed to condense inside the trap, under static vacuum. The liquid nitrogen bath was then removed from the trap (volume=73 ml), and the contents of the trap were allowed to warm to 22° C., in order to cause the excess Br$_2$ to react. The resulting mixture, consisting of CF$_3$—N(Br)—OCF$_2$CF$_3$, BrCH$_2$CH$_2$Br, and unreacted CH$_2$=CH$_2$, was then fractionated, under dynamic vacuum conditions, through a series of traps at −55° C., −135° C. and −196° C., with the product CF$_3$—N(Br)—OCF$_2$CF$_3$ (0.99 mmol, yield 99%) condensing inside the trap at −135° C.

CF$_3$—N(Br)—OCF$_2$CF$_3$ was characterized as follows:

IR (2 torr, cell with AgCl plates): 1390(m), 1269(vs), 1241(vs), 1214(s), 1184(vs), 1097(vs), 948(m), 876(m), 848(w), 754(m), 723(m), 664(m), 634(vw), 520(vw) cm$^{-1}$.

$^{19}F$—NMR $CF_3{}^C N(Br)-OCF^A F^B CF_3{}^D$ (CCl$_4$, (CD$_3$)$_2$SO, coaxial, 24° C.): δA −95.4, B −98.9 (2F, very broad typical AB pattern, A and B are the highest values of very broad peaks), C −75.1 (3F, t), D −85.2 ppm (3F, t), $J_{AB}$=not determined, $J_{AC}=J_{BC}=3.0$, $J_{AD}=J_{BD}=1.6$, $J_{CD}=0$. In order to determine the values δA, δB and $J_{AB}$, a low-temperature spectrum was recorded in CDCl$_3$ at −30° C. The variable temperature unit was a Bruker B-VT 1000 with a "factory-specified" precision of ±0.5 K.

Under these conditions, the N.M.R. spectrum is as follows: δA −94.8 (d-q-q), B −99.3 (d), C −74.7 (d), D −84.9 ppm (t), $J_{AB}=141.8$, $J_{AC}=5.1$, $J_{AB}=J_{BD}=1.4$, $J_{BC}=J_{CD}=0$ Hz.

Mass spectrum major m/z (EI): 297/299 (M$^+$), 218 (M-Br$^+$), 178/180 (CF$_3$=NBrO$^+$), 164 (CF$_3$NBr$^+$), 130 (CF$_3$NOCF$^+$), 119 (CF$_2$CF$_3{}^+$), 79/81 (Br$^+$), 69 (CF$_3{}^+$), 64 (CF$_2$=N$^+$), 50 (CF$_2{}^+$); 47 (COF$^+$);

major m/z (CI): 298/300 (M+1$^+$), 278/280 (M+1-HF$^+$), 218 (M+1HBr$^+$), 164 (CF$_3$NBr$^+$), 199 (CF$_3$CF$_2{}^+$).

EXAMPLE 6

This example describes the preparation of

by starting from $CF_2=N-OCF_2CF_3$ and F$_2$.

The reaction vessel was a Hoke bomb of stainless steel having a capacity of 150 ml, equipped with a Nupro SS-4JBR valve. To the bomb a vacuum of 5 microns Hg was applied (while the same vacuum was employed throughout the subsequent operating steps to be carried out under vacuum) and then, 1 atm of F$_2$ was charged through a manifold of stainless steel, in order to passivate the equipment.

After 3 hours at 22° C., F$_2$ was evacuated.

Then, before use, commercial F$_2$ (Air Products) was made to flow through an NaF scrubber.

The passivated bomb was cooled down to −196° C., and CF$_2$=N—OCF$_2$CF$_3$ (1.00 mmol) was condensed, by means of a static vacuum, through a vacuum line of Pyrex glass. The reactor was then put into communication with the stainless steel line, and F$_2$ (1.05 mmol, a 5% excess) was added, still operating at the temperature of liquid nitrogen.

The bomb was then placed inside a cold empty Dewar bottle, from which liquid nitrogen had been removed shortly before; the upper end of the Dewar bottle was covered with an aluminum foil. The temperature of the reactor increased from −196° C. to 22° C. during a time period of about 17 hours.

The reactor was then removed from the Dewar bottle, and was left standing at 23° C. for 6 hours.

The bomb was then cooled again with liquid nitrogen, and a trace of volatile matter was pumped off at −196° C.

Then, with the bomb being maintained at 23° C., the volatile contents were pumped into a "U"-shaped Pyrex trap cooled with liquid nitrogen. The fractionation, under dynamic vacuum, through a series of traps cooled at −100° C., −135° C. and −196° C., supplied $$CF_3-N(F)-OCF_2CF_3$$

(0.84 mmol, yield 84%) inside the trap at −135° C. Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Fluorinated alkoxy-imines comprising the formula:

$$R_x-CF=N-O-CZ_1Z_2-CF_3 \qquad (I)$$

wherein:
   $R_x$ is either F or a perhalogenated alkyl group containing from 1 to 3 carbon atoms, and
   $Z_1$ and $Z_2$, either equal to, or different from, each other, are F, Cl, Br or H.

2. Fluorinated alkoxy-imines according to claim 1, wherein $R_x$ is either F or a perfluorinated alkyl group containing from 1 to 3 atoms.

3. Fluorinated alkoxy-imines according to claim 2, comprising the formula:

$$CF_2=N-O-CFZ-CF_3 \qquad (I')$$

wherein Z represents F, Cl or H.

* * * * *